United States Patent
Mohapatra et al.

(10) Patent No.: US 11,198,842 B1
(45) Date of Patent: Dec. 14, 2021

(54) MICROFLUIDIC-COUPLED IN VITRO MODEL OF THE BLOOD-BRAIN BARRIER

(71) Applicant: University of South Florida, Tampa, FL (US)

(72) Inventors: Subhra Mohapatra, Lutz, FL (US); Shyam S. Mohapatra, Lutz, FL (US); Tao Wang, Tampa, FL (US); Taylor Martinez, Tampa, FL (US)

(73) Assignee: University of South Florida, Tampa, FL (US)

( * ) Notice: Subject to any disclaimer, the term of this patent is extended or adjusted under 35 U.S.C. 154(b) by 117 days.

(21) Appl. No.: 16/799,428

(22) Filed: Feb. 24, 2020

Related U.S. Application Data

(60) Provisional application No. 62/809,271, filed on Feb. 22, 2019.

(51) Int. Cl.
| | |
|---|---|
| *C12M 3/00* | (2006.01) |
| *B01L 3/00* | (2006.01) |
| *C12M 3/06* | (2006.01) |
| *C12M 1/12* | (2006.01) |
| *C12N 5/071* | (2010.01) |

(52) U.S. Cl.
CPC ............ *C12M 23/16* (2013.01); *C12M 25/04* (2013.01); *C12N 5/0697* (2013.01)

(58) Field of Classification Search
CPC ....... C12M 23/12; C12M 25/02; C12M 23/16
See application file for complete search history.

(56) References Cited

U.S. PATENT DOCUMENTS

| | | | |
|---|---|---|---|
| 2012/0003732 A1* | 1/2012 | Hung | C12M 41/36 435/289.1 |
| 2014/0030752 A1* | 1/2014 | Cuiffi | C12M 21/08 435/29 |

(Continued)

FOREIGN PATENT DOCUMENTS

WO  2017035119 A1  3/2017

OTHER PUBLICATIONS

Brown, Jacquelyn A. et al. Recreating blood-brain barrier physiology and structure on chip: A novel neurovascular microfluidic bioreactor. Biomicrofluidics 9, 054124 (2015); https://doi.org/10.1063/1.4934713.

(Continued)

*Primary Examiner* — Nathan A Bowers
(74) *Attorney, Agent, or Firm* — Smith & Hopen, P.A.; Paul Murty

(57) ABSTRACT

An in vitro microfluidic device includes a device configured to model a blood-brain barrier. The device includes a center well in fluidic communication with each of an inlet and an outlet. Each of the center well, inlet, and outlet includes a porous membrane that separates a "blood" portion (a fluid flow portion) from a "brain" portion (a fluid containing portion). The porous membrane is seeded with endothelial cells such as the human venule endothelial cells (HUVECs) on the blood side, and with astrocytes on the brain side, to accurately model the blood-brain barrier. Fluid flows between the inlet, the center well, and the outlet to test the permeability of the porous membrane, thereby providing an accurate in vitro model of a blood-brain barrier.

17 Claims, 9 Drawing Sheets

(56) References Cited

U.S. PATENT DOCUMENTS

2014/0057311 A1* 2/2014 Kamm .................. C12M 25/14
                                                                                         435/29
2018/0017586 A1* 1/2018 Levner .............. B01L 3/502761
2018/0305651 A1 10/2018 Kerns et al.

OTHER PUBLICATIONS

Jeong, Sehoon et al. A Three-Dimensional Arrayed Microfluidic Blood-Brain Barrier Model with Integrated Electrical Sensor Array. IEEE Transactions on Biomedical Engineering, vol. 65, No. 2, Feb. 2018, pp. 431-439.

Wang, Jack D. et al. Organization of Endothelial Cells, Pericytes, and Astrocytes into a 3D Microfluidic in Vitro Model of the Blood-Brain Barrier. Molecular pharmaceutics, 2016; 13(3), pp. 895-906; doi: 10.1021/acs.molpharmaceut.5b00805.

Yeste, J. et al. A novel strategy to monitor microfluidic in-vitro blood-brain barrier models using impedance spectroscopy. Proc. SPIE 9518, Bio-MEMS and Medical Microdevices II, 95180N (Jun. 1, 2015); doi: 10.1117/12.2180567.

* cited by examiner

MICROFLUIDIC-COUPLED IN VITRO MODEL OF THE BLOOD-BRAIN BARRIER

CROSS-REFERENCE TO RELATED APPLICATIONS

This nonprovisional application is a continuation of and claims priority to provisional application No. 62/809,271, entitled "Microfluidic-coupled in Vitro Model of the Blood-Brain Barrier," filed on Feb. 22, 2019, including at least one common joint inventor, the entirety of which is incorporated herein by reference.

BACKGROUND OF THE INVENTION

1. Field of the Invention

This invention relates, generally, to the blood-brain barrier. More specifically, it relates to a microfluidic-coupled in vitro blood-brain barrier model that more accurately models the blood-brain barrier for the purpose of improving drug discovery for brain disorders in regard to the permeability of drugs or substances across the blood-brain barrier.

2. Brief Description of the Prior Art

Microfluidic devices for modeling human physiology are becoming increasingly important in biological research. The blood-brain barrier (BBB) is a highly selective, semipermeable barrier that separates circulating blood from the brain and extracellular fluid in the central nervous system. [1]. Currently, in vitro modeling of the BBB is limited to insert systems such as those marketed under the trade name TRANSWELL®, which provide pores for fluid transfer. However, existing insert systems fail to adequately model crucial aspects of the BBB, such as shear stress. Such drawbacks lead to poor translation to in vivo BBB studies and tests, thereby resulting in poor research outcomes in terms of drug efficacy.

Attempts have been made to provide improved microfluidic devices to more accurately represent the BBB, such as those disclosed in U.S. Publication No. 20180305651 and International Publication No. WO 2017035119. However, while the attempts are directed at improving in vitro models of the BBB, and in particular the permeability of the model BBB, these attempts fail to include equilibrium-directed fluid conduits connecting inlets, center wells, and outlets. For at least these reasons, the prior art attempts to provide accurate BBB models that have failed to accurately model the BBB, and thereby fail to provide accurate research results for drugs or substances tested on these models.

Accordingly, what is needed is a more accurate physiological model of the BBB utilizing organ-on-a-chip technologies. For example, by placing human umbilical vein endothelial cells (HUVECs) or brain-derived endothelial cells, astrocytes, and pericytes together in a culture, a model blood-brain barrier can be established.

However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a simple and accurate in vitro model of a blood-brain barrier is now met by a new, useful, and non-obvious invention.

The novel in vitro device includes a device including a center well in fluidic communication with each of an inlet and an outlet. Each of the center well, inlet, and outlet includes a bottom surface that is a porous membrane and a fluid containing portion extending away from the porous membrane. The porous membrane of the center well separates a fluid flow side from the fluid containing portion. The fluid flow side is configured to mimic a blood side of a blood-brain barrier, the fluid containing portion is configured to mimic a brain side of the blood-brain barrier. The fluid flow side of the porous membrane of the center well including a plurality of human umbilical vein endothelial cells (HUVECs) disposed on the porous membrane, and the fluid containing portion of the center well including a plurality of astrocytes disposed therein. The HUVECs and the astrocytes disposed on opposing sides of the porous membrane of the center well are configured to decrease a permeability of the porous membrane of the center well, thereby accurately modeling the blood-brain barrier.

The center well, the inlet, and the outlet form a closed system via the first plurality of fluid conduits and the second plurality of conduits, such that an equilibrium of fluid flowing through the closed system is accomplished. The closed system is capable of bidirectional fluid through the first and second plurality of conduits. In an embodiment, the porous membrane of the center well has a thickness of approximately 120 μm. The porous membrane of the center well may include a plurality of pores each having a diameter of approximately 0.4 μm.

The in vitro device also includes a first plurality of fluid conduits fluidically coupling the inlet to the center well on the fluid flow side of the center well, such that the first plurality of fluid conduits span from the porous membrane of the inlet to the porous membrane of the center well. In addition, the in vitro device includes a second plurality of fluid conduits fluidically coupling the outlet to the center well on the fluid flow side of the center well, such that the second plurality of fluid conduits span from the porous membrane of the center well to the porous membrane of the outlet. The first and second plurality of fluid conduits, together with the center well, the inlet, and the outlet, form a closed system.

In an embodiment, one or more of the first plurality of fluid conduits and/or the second plurality of fluid conduits is arranged in an oscillating pattern. In an oscillating pattern, a length of the given fluid conduit from a first end to a second end (for example, from a first end disposed at the inlet to a second end disposed at the center well) is greater than a lateral distance between the first end and the second end (for example, the distance between the inlet and the center well is much smaller than a length of the fluid conduit, due to the oscillating pattern of the fluid conduit).

In an embodiment, the device is disposed on an insert coupled to a chip including a plurality of testing wells. As such, the device is configured to test the permeability of the porous membrane of the center well via a fluid transferred from the plurality of testing wells on the flow chip to the device on the insert. The insert may include a plurality of devices having the characteristics described above.

An object of the invention is to provide a more accurate model of a BBB in a simple design, such that fluids can be accurately tested and researched for permeability across the model BBB in vitro prior to in vivo testing.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes the manufacture and use of a BBB model that has greater accuracy than prior art models, such as those marketed under the trade name TRANSWELL®. The model includes a center well fluidically coupled to each of an inlet and an outlet via a plurality of fluid conduits, with the inlet and the outlet disposed on opposing sides of the center well. The each of the plurality of fluid conduits is arranged in an oscillating pattern with body sections thereof disposed adjacent to and overlapping with each other, ensuring the controlled flow of fluid from the inlet to the center well, and from the center well to the outlet. In addition, the center well includes a porous membrane, through which at least a portion of the fluid permeates. The BBB model experiences greater control of fluid permeation, thereby more accurately representing real-life BBBs in real-life patients, allowing for more accurate research into drug permeation across the BBB.

Figure 1:
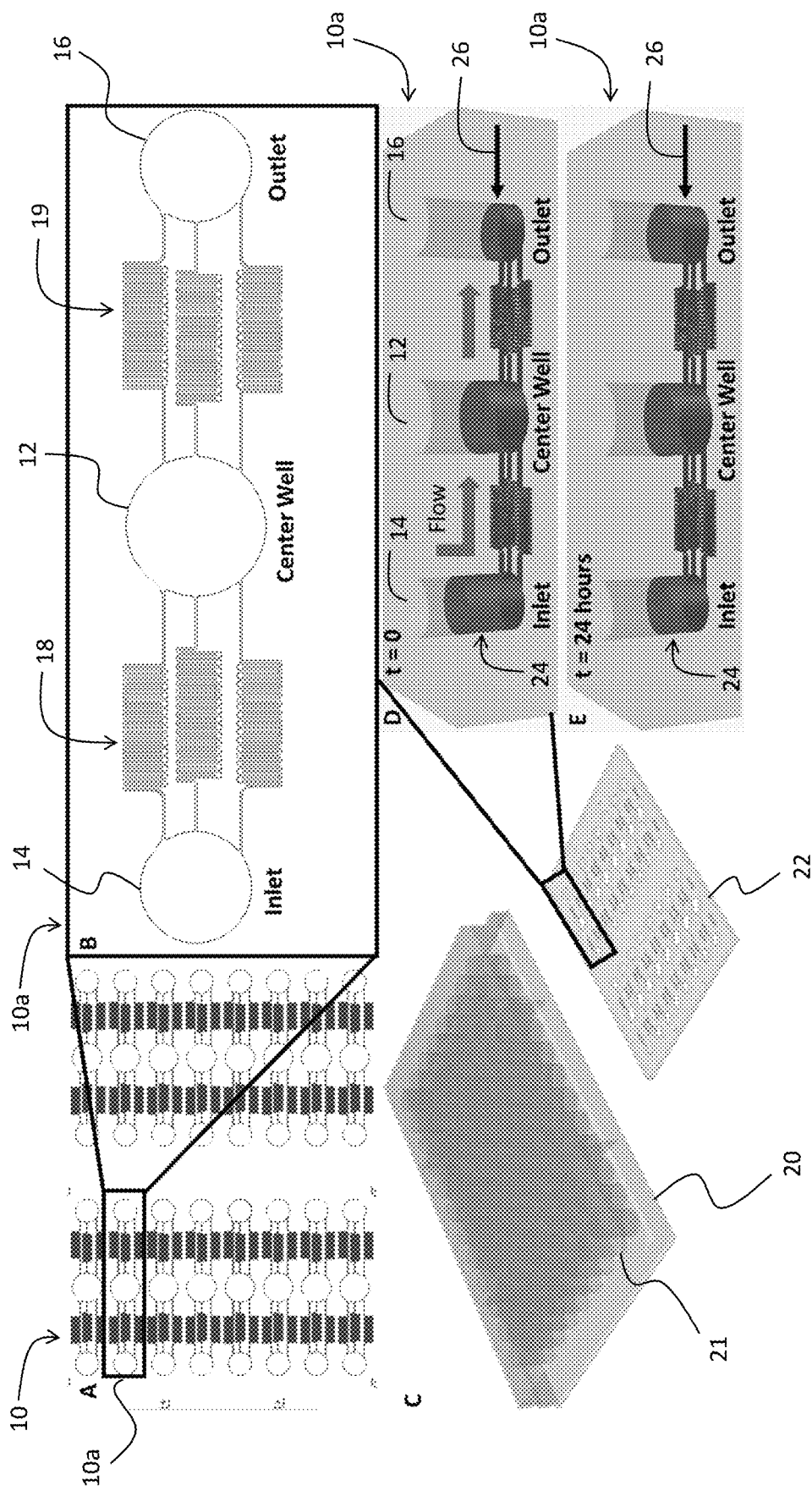
FIG. 1 depicts a model of a blood-brain barrier, including a mask used to generate an insert including a plurality of devices in section A; a close up view of an individual device in section B; a chip and insert combined system in section C; an initial fluid configuration of the individual device in section D; and a fluid configuration after a period of time of the individual device in section E.

Accordingly, as shown in FIG. 1, a plurality of devices marked as 10 (alternatively referred to as bioreactors 10) are disposed on an insert 22, which is designed to be combined with a flow chip 20 (alternatively referred to as chip 20 or microfluidic chip 20) in a BBB model for researching fluids disposed within chip 20, which includes a plurality of testing wells 21. Each of the plurality of devices marked as 10, such as device 10a, includes center well 12 in fluidic communication with each of inlet 14 and outlet 16. The fluidic communication is accomplished via a first plurality of fluid conduits 18 connecting center well 12 with inlet 14, as well as via a second plurality of fluid conduits 19 connecting center well 12 with outlet 16. As such, inlet 14 is indirectly fluidically coupled to outlet 16 via center well 12, first plurality of fluid conduits 18, and second plurality of fluid conduits 19.

Fluid flow can be accomplished throughout the system including inlet 14, center well 12, and outlet 16 via each of the plurality of fluid conduits 18, 19, creating a system in which fluidic equilibrium can be achieved. To aid in creating an equilibrium between inlet 14, center well 12, and outlet 16, each of the first and second plurality of fluid conduits 18, 19 is arranged in an oscillating pattern. Said another way, each conduit has a length that is much greater than a lateral distance separating a first end of the conduit from a second end of the conduit. As such, each conduit is arranged such that the conduit coils in an oscillating pattern between the first end and the second end. As a result, the body of the conduit includes substantially equally sized portions that are adjacent to each other between opposing ends of the conduit, as shown in particular in section B of FIG. 1.

The equilibrium of fluid flow discussed above is shown in particular in sections D and E of FIG. 1. As shown in section D of FIG. 1, at an initial time (i.e., t=0), inlet 14 includes a greater amount of fluid 24 than an amount of fluid 24 in either center well 12 or outlet 16. Arrow 26 in section D of FIG. 1 denotes a level of fluid 24 disposed within outlet 16 at the initial time, t=0. As shown in section E of FIG. 1, at a final time (i.e., t=24 hours), each of inlet 14, center well 12, and outlet 16 includes a substantially equal amount of fluid 24. Moreover, as shown in section E of FIG. 1, at the final time, arrow 26 denotes the initial level of fluid 24 disposed within outlet 16, showing in particular the increase in fluid 24 disposed within outlet 16 during the fluid flow process. The equilibrium accomplished within device 10a is accomplished by fluid flow between inlet 14, center well 12, and outlet 16, via first plurality of fluid conduits 18 and second plurality of fluid conduits 19, as described in detail above.

Figure 2:
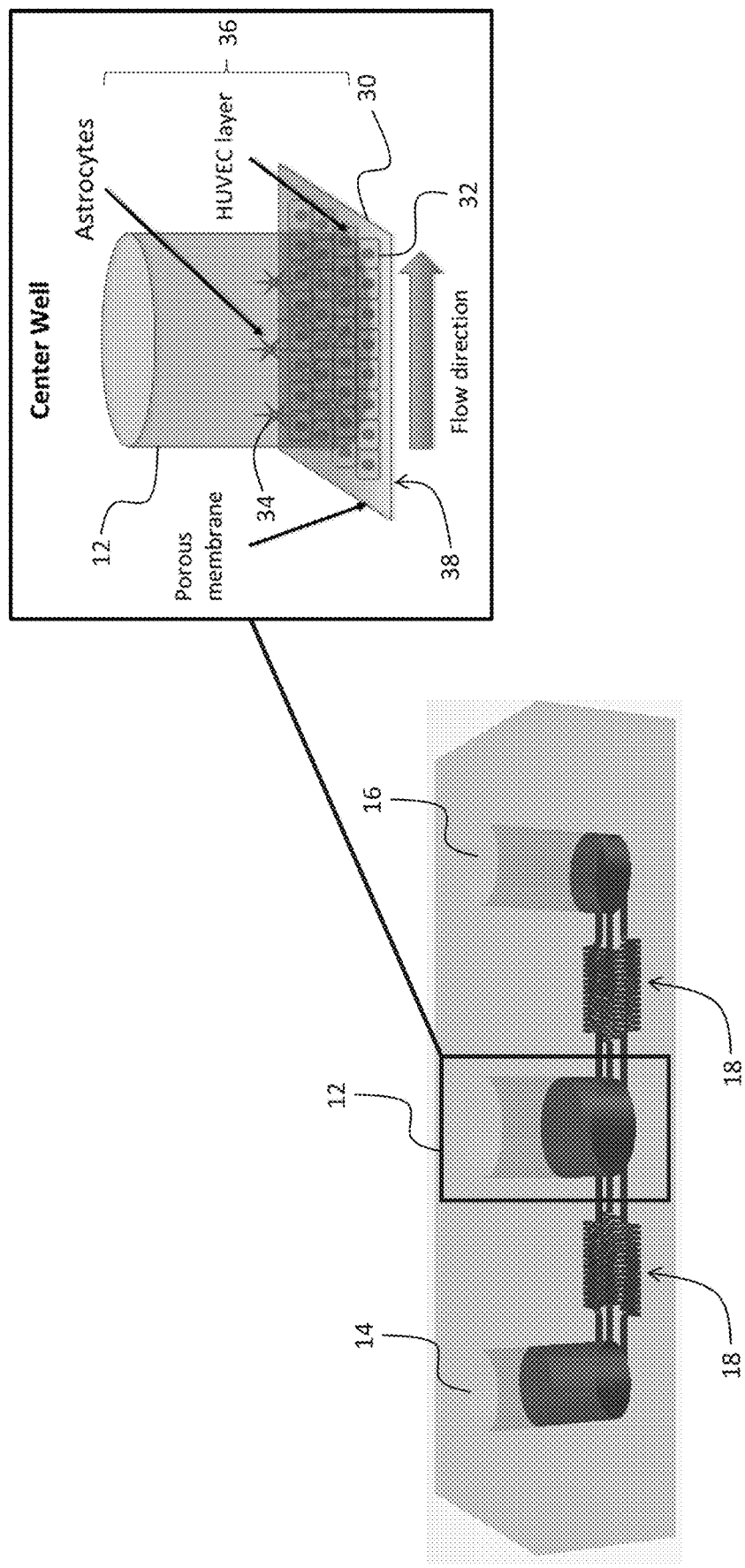
FIG. 2 is a perspective view of an individual device, including a close-up view of a center well of the individual device.

As shown in FIG. 2, center well 12 includes a porous membrane 30 forming a bottom surface of center well 12, with a fluid containing portion (or vessel) of center well 12 (denoted as reference numeral 36 in FIG. 2, which is designed to mimic a "brain" side of membrane 30) extending away from membrane 30. Membrane 30 separates the brain side 36 of center well 12 from a fluid flow portion of the system (denoted as reference numeral 38 in FIG. 2, which is designed to mimic a "blood" side of membrane 30). The first plurality of fluid conduits 18 and the second plurality of fluid conduits 19 are in fluidic communication with porous membrane 30, such that fluid 24 can flow into center well 12 via capillary flow. Porous membrane 30 is lined on blood side 38 with a HUVEC layer 32 seeded thereon. Brain side 36 of membrane 30 includes a plurality of astrocytes 34 to mimic a brain side of a real-life BBB. In an embodiment, porous membrane 30 has a thickness of approximately 120 µm±15%, with pores each having a diameter of approximately 0.4 µm±15%. Each of inlet 14 and outlet 16 are similar in structure to center well 12, with each of inlet 14 and outlet 16 including a porous membrane 30 forming a bottom surface thereof, with a fluid containing portion, of vessel, of inlet 14 and outlet 16 extending away from respective membranes 30.

Figure 3:
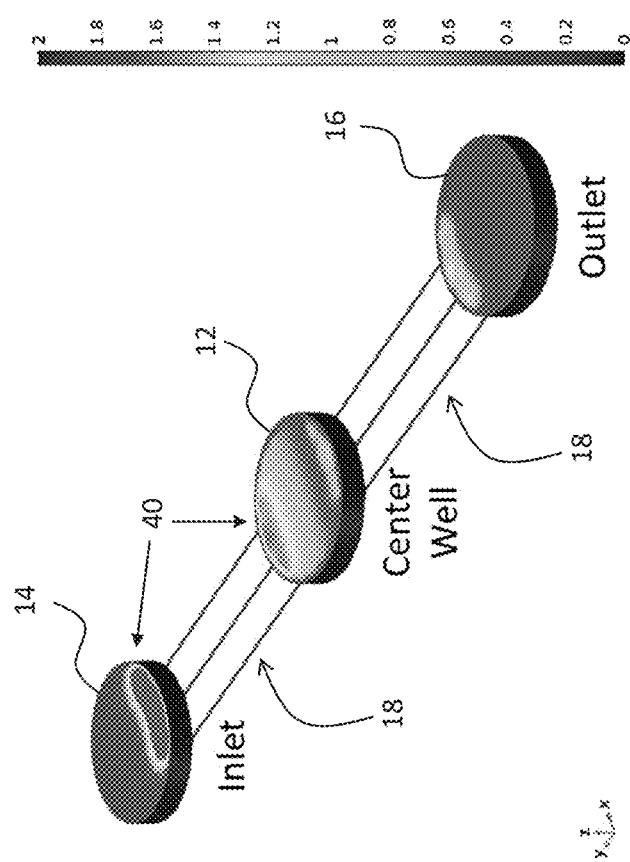
FIG. 3 depicts the average shear stress experienced across the membranes of each of the inlet, center well, and outlet of an individual device.

FIG. 3 depicts the average shear stress experienced across each porous membrane 30 of one of the plurality of devices marked as 10 from inlet 14 to outlet 16, with the shear stress measured over a period of time, such as 24 hours. As shown in FIG. 3, porous membrane 30 of center well 12 experiences shear stress across the entirety of center well 12, with the membrane of inlet 14 experiencing a greater degree of shear stress on a side proximate to center well 12, and the membrane of outlet 16 experiencing a small degree of shear stress on a side proximate to center well 12. In a real-life BBB, shear stress is a tangential force across a surface of the barrier membrane resulting from fluid flow along the membrane. Shear stress is essential to a healthy and functional real-life BBB because the shear stress forces reduce the permeability of the BBB, resulting in a decrease of harmful fluid flow across the BBB. [2]. In addition, shear stress mechanically induces the upregulation of tight junctional proteins. [3]. The shear stress experienced by each of inlet 14, center well 12, and outlet 16 as depicted in FIG. 3 is measured in dyne per square centimeter, or $dyn/cm^2$; 1 $dyn/cm^2$ is equal to 0.1 pascals. As such, the scale shown in FIG. 3 spans from 0 $dyn/cm^2$ to 2 $dyn/cm^2$, or from 0 pascals to 0.2 pascals. The shear stress is concentrated on the portion of inlet 14 that is proximate to, or closest to, center well 12, as well as the portion of center well 12 that is proximate to, or closest to, inlet 14. The concentration of shear stress on the membranes of inlet 14 and center well 12 is denoted by reference numeral 40 in FIG. 3.

Example 1

Figure 4:
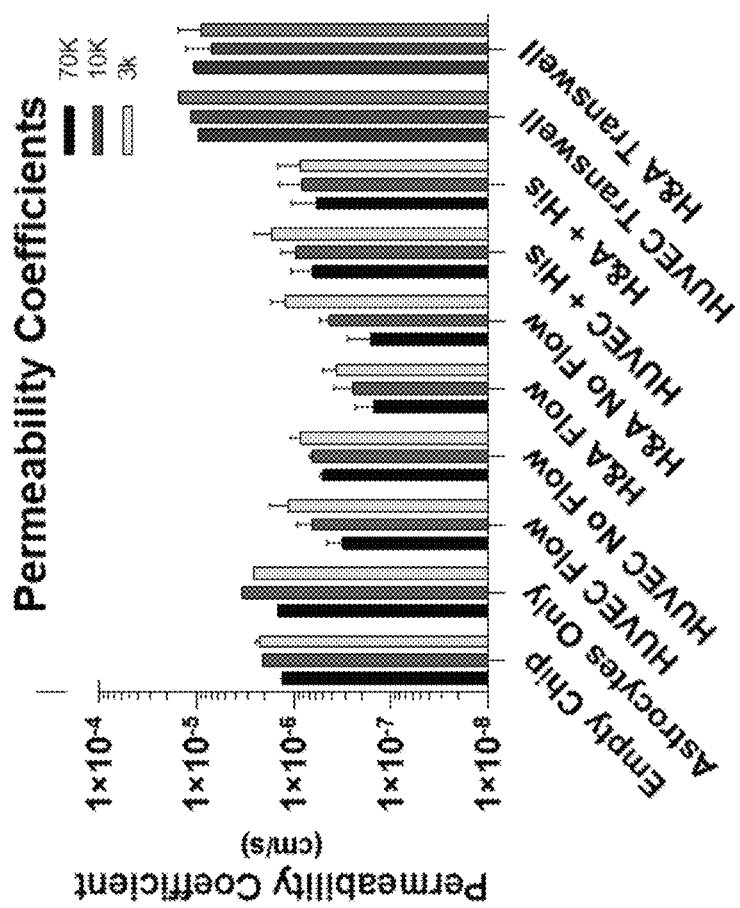
FIG. 4 is a graphical representation of the permeability coefficients of chips under a variety of conditions, as compared with prior art chips marketed under the trade name TRANSWELL®.

As shown in FIG. 4, flow chip 20 was tested under a variety of conditions and compared with prior art chips marketed under the trade name TRANSWELL®. The graph of FIG. 4 depicts the paracellular permeability coefficients measured in cm/s for various membrane conditions, measured by flowing fluorescent dextran molecules at molecular weights of 70 kDa (kilodaltons), 10 kDa, and 3 kDa. The testing conditions included an empty chip 20 including no cells thereon; an astrocytes-only chip 20, with astrocytes 34 on the brain side 36 of the membrane 30; a HUVEC flow chip 20, including HUVECs on the blood side 38 of the membrane 30 and regular flow conditions of fluid 24; a HUVEC no-flow chip 20, including HUVECs on the blood side 38 of the membrane 30 and low flow conditions of fluid 24; a H&A flow chip 20, including HUVECs on the blood side 38 of the membrane 30, as well as astrocytes 34 on the brain side 36 of the membrane 30, under regular flow conditions of fluid 24; a H&A no-flow chip 20, including HUVECs on the blood side 38 of the membrane 30, as well as astrocytes 34 on the brain side 36 of the membrane 30, under low-flow conditions of fluid 24; a HUVEC+His chip 20, including HUVECs on the blood side 38 of the membrane 30 with approximately 40 µM of histamine added to the media to disrupt tight junctions from forming on the membrane 30, under regular flow conditions of fluid 24; a H&A+His chip 20, including HUVECs on the blood side 38 of the membrane 30, astrocytes 34 on the brain side 36 of the membrane 30, and approximately 40 µM of histamine added to the media to disrupt tight junctions from forming on the membrane 30, under regular flow conditions of fluid 24; a HUVEC TRANSWELL® chip, including HUVECs on the blood side of the TRANSWELL® culture membrane; and a H&A TRANSWELL® chip, including HUVECs on the blood side of the TRANSWELL® culture membrane, as well as astrocytes on the brain side of the TRANSWELL® culture membrane.

Testing was performed by completing a two-way analysis of variance (ANOVA) test at a significance level a of 0.05, as well as Tukey's post hoc tests at a significance level a of 0.05 to identify individual differences between tested flow chips. The flow chips were compared to each other within the same molecular weight, such that each chip is compared for permeability of 70 kDa molecules, 10 kDa molecules, and 3 kDa molecules separately.

The results depicted in FIG. 4 show that chip 20 outperforms similar chips that are currently available and marketed under the trade name TRANSWELL® for the molecular weights tested. Specifically, each testing condition of flow chip 20 (i.e., each HUVEC and H&A flow chip) resulted in a decreased permeability coefficient as compared with the prior art chips (it should be noted that the control flow chips, i.e. the empty chip and the flow chip with only astrocytes, are not statistically different from prior art flow chips). As such, each iteration of flow chip 20 had a decreased diffusion rate across membrane 30 as compared with prior art membranes. Within the tested flow chips themselves, chip 20 including both HUVECs on the blood side 38 of the membrane 30, as well as astrocytes 34 on the brain side 36 of the membrane 30, under regular flow conditions of fluid 24 performed the best.

Example 2

Figure 5:
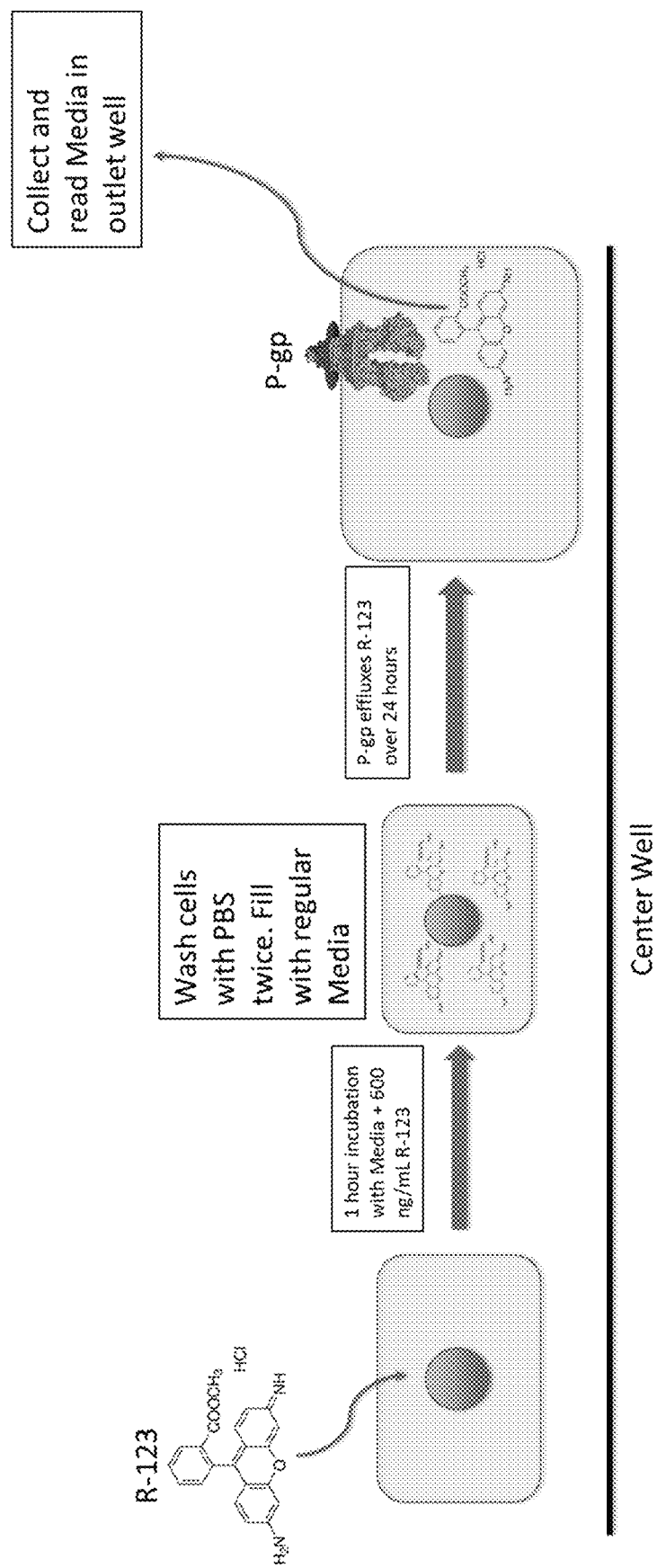
FIG. 5 depicts methods of fluid flow through the model of the BBB, in accordance with an embodiment of the present invention.

To further test the three most successful versions of chip 20 (i.e., the HUVEC flow chip, the H&A flow chip, and the H&A no-flow chip), the plurality of devices 10 were subjected to rhodamine-123 (R-123) to test for the efflux activity of p-glycoprotein (p-gp) in tested flow chips. P-glycoprotein is a plasma membrane protein used to transport substances across membrane. As shown in FIG. 5, each flow chip 20 was tested by incubating flow chip 20 for one hour with a regular media and 600 ng/mL of R-123. Each flow chip was then washed with PBS (phosphate buffered saline) twice, and the plurality of devices 10 were then filled with regular media. Over the subsequent 24 hours, P-gp effluxes R-123, and the final media in outlet 16 is collected and analyzed.

Figure 6:
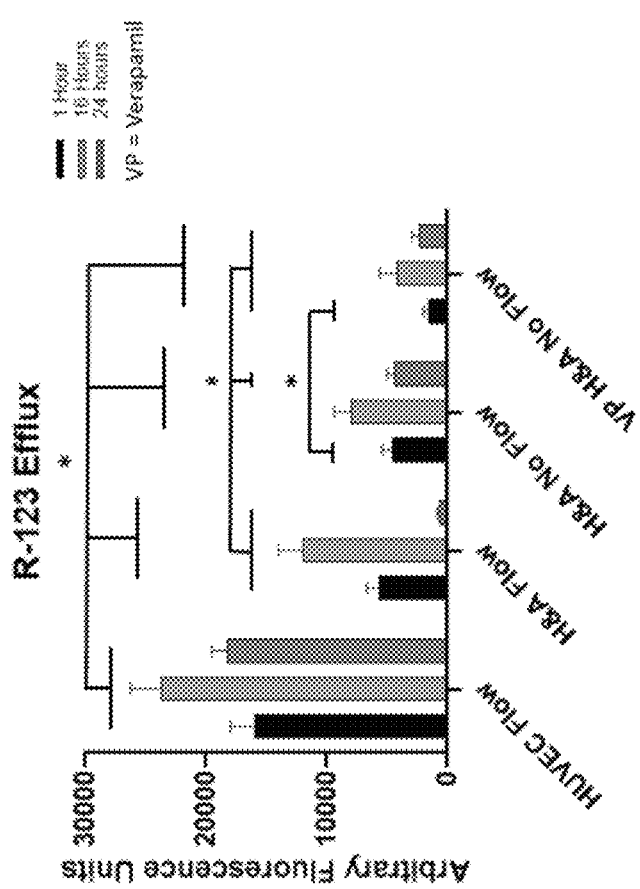
FIG. 6 is a graphical representation of fluids collected from the method of FIG. 5 using flow chips under a variety of conditions.

FIG. 6 shows the results of the test depicted in FIG. 5 for variations of flow chip 20: a HUVEC flow chip 20, including HUVECs on the blood side 38 of the membrane 30 and regular flow conditions of fluid 24; a H&A flow chip 20, including HUVECs on the blood side 38 of the membrane 30, as well as astrocytes 34 on the brain side 36 of the membrane 30, under regular flow conditions of fluid 24; a H&A no-flow chip 20, including HUVECs on the blood side 38 of the membrane 30, as well as astrocytes 34 on the brain side 36 of the membrane 30, under low flow conditions of fluid 24, and a H&A no-flow chip 20, including HUVECs on the blood side 38 of the membrane 30, as well as astrocytes 34 on the brain side 36 of the membrane 30, with verapamil used to inhibit p-gp, under low flow conditions of fluid 24. R-123 values were measured at 1 hour, 16 hours, and 24 hours, with the values recorded in arbitrary fluorescence units that measure the intensity of fluorescents in the measured media. Testing was performed by completing a two-way analysis of variance (ANOVA) test at a significance level a of 0.05, as well as Tukey's post hoc tests at a significance level a of 0.05 to identify individual differences between tested chips.

As the graph in FIG. 6 depicts, flow chip 20 including regular flow conditions and only HUVECs, without astrocytes, experienced significantly increased p-gp efflux as compared with the other flow chips, indicating a higher level of permeability. The H&A flow chip 20 was measured to be statistically significant from the H&A no-flow chip 20 including verapamil at all time points, and statistically different from the H&A no-flow chip 20 without verapamil at 24 hours. The H&A no-flow chip 20 was measured to be statistically different from the H&A no-flow chip 20 including verapamil at only 1 hour. These results indicate that over 24 hours, the H&A flow chip 20 including both HUVECs on the blood side 38 of the membrane 30, as well as astrocytes 34 on the brain side 36 of the membrane 30, under regular flow conditions of fluid 24 performed the best, similar to the results in the Example 1 section above.

Example 3

Figure 7:
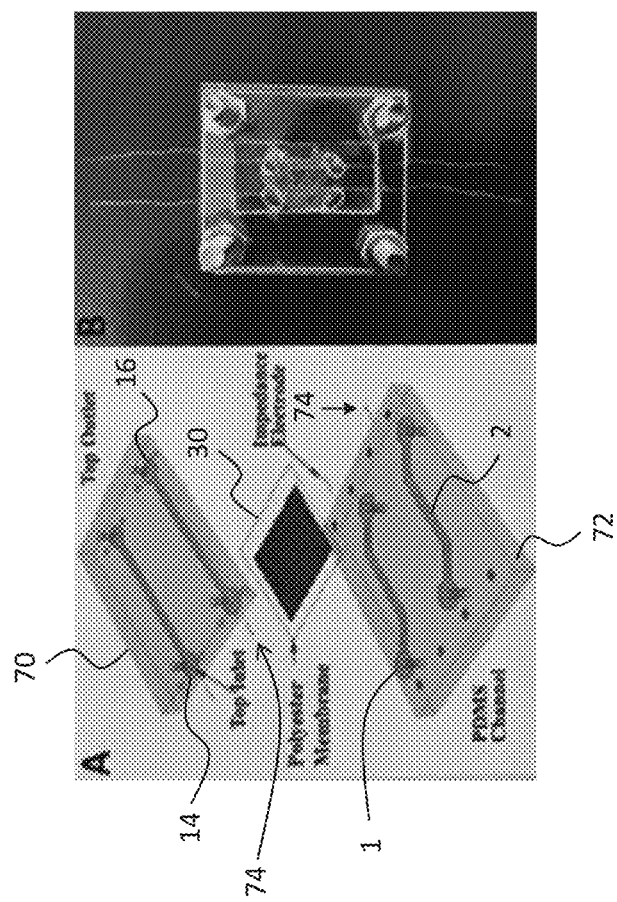
FIG. 7 is a perspective view of a BBB-on-a-chip design, in accordance with an embodiment of the present invention.

In an embodiment, chip 20 and insert 22 are manufactured by curing polydimethylsiloxane (PDMS) on a predesigned photolithography mask. Microfluidic chip 20 is assembled including top channel 70 and bottom channel 72, as shown in sections A and B of FIG. 7. The microfluidic chip also includes membrane 30 that is 10 µm thick, with a pore size of 0.4 µm. Silver chloride (Ag/Cl) electrodes 74 are included on microfluidic chip 20 and placed on each side of membrane 30 (i.e., separate electrodes 74 are disposed proximate to top channel 70 and proximate to bottom channel 72). Each of top channel 70 and bottom channel 72 is coated with 0.01% fibronectin. Microfluidic chip 20 is seeded with HUVEC (approximately 300-350 cells/cm$^2$) in top channel 70. Primary astrocytes and/or primary pericytes are seeded into bottom channel 72.

Figure 8:
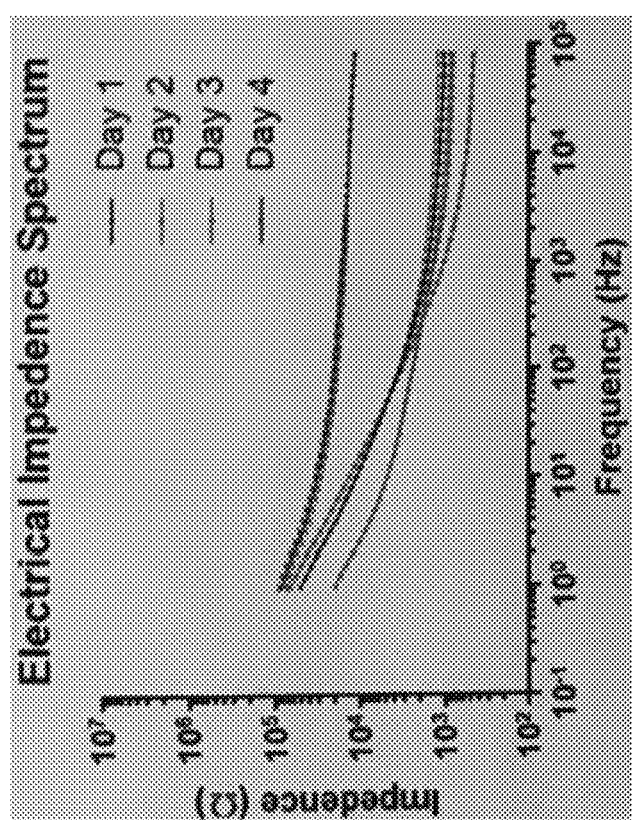
FIG. 8 is a graphical representation of an electrical impedance spectrum of the BBB-on-a-chip design of FIG. 7 across four days of testing, showing an increase in electrical impedance across a broad frequency range on the final day of testing.

As graphically depicted in FIG. 8, electrical impedance spectroscopy measurements were taken across a range of frequencies on four consecutive days. For each of the days, as the frequency increased (measured in hertz), impedance decreased (measured in ohms). The greatest impedance values recorded over the range of frequencies occurred on the final day of testing, day 4, indicating that electrical impedance increased over time for chip 20. Importantly, the permeability of microfluidic chip 20 is indirectly proportional to the electrical impedance, such that permeability decreases as impedance increases. Accordingly, the maximum impedance values measured on the final day of testing indicates a decrease in permeability of microfluidic chip 20, making this chip 20 an ideal in vitro model of the BBB.

Figure 9:
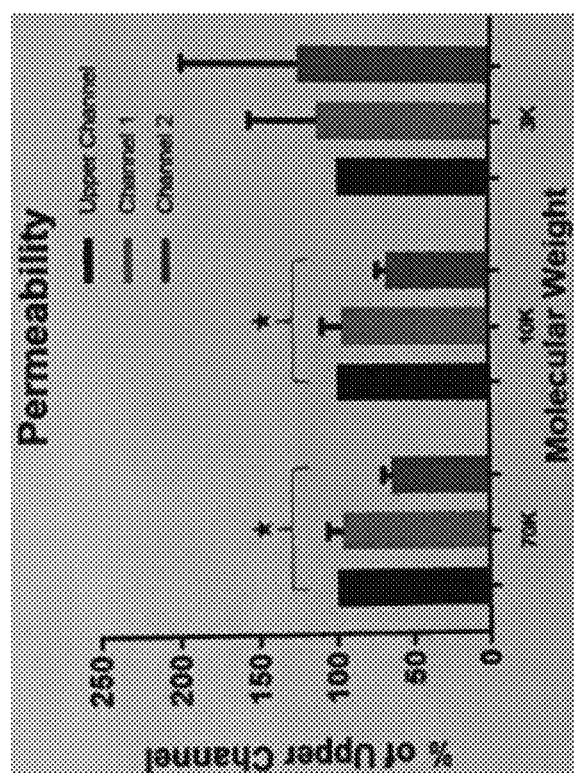
FIG. 9 is a graphical representation of permeability changes between channels of the blood-brain barrier-on-a-chip design of FIG. 7 for molecules of different weights.

Accordingly, as graphically depicted in FIG. 9, the permeability of microfluidic chip 20 was measured by flowing fluorescent dextran molecules at molecular weights of 70 kDa, 10 kDa, and 3 kDa into top channel 70. After four hours, the amount of molecules in each of top channel 70 and bottom channel 72 (including channel 1 and channel 2) was measured and compared. As shown in FIG. 9, the permeability of channel 2 was reduced for the fluorescent dextran molecules at molecular weights of 70 kDa and 10 kDa, but was not reduced for the molecules at a molecular weight of 3 kDa. In addition, the permeability of channel 1 did not change in a statistically significant way for any of the molecular weights tested.

REFERENCES

[1] Daneman, R. & Prat, A. *The Blood-Brain Barrier*. Cold Spring Harb. Perspect. Biol. 7(1). (2015).
[2] Cucullo, L. et al. *The role of shear stress in Blood-Brain Barrier endothelial physiology*. BMC Neurosci. 12(40). (2011).
[3] Jeong, S. et al. *A Three-Dimensional Arrayed Microfluidic Blood-Brain Barrier Model with Integrated Electrical Sensor Array*. IEEE Transactions on Biomedical Engineering. 65(2), 431-439. (2018).

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An in vitro device configured to model a blood-brain barrier, the device comprising:
    a center well in fluidic communication with each of an inlet and an outlet, each of the center well, inlet, and outlet including an independent bottom surface that is a porous membrane and a fluid containing portion extending away from the porous membrane;
    the porous membrane of the center well separating a fluid flow side from the fluid containing portion, the fluid flow side configured to mimic a blood side of a blood-brain barrier, the fluid containing portion configured to mimic a brain side of the blood-brain barrier;

the fluid flow side of the porous membrane of the center well including a plurality of human endothelial cells disposed on the porous membrane, and the fluid containing portion of the center well including a plurality of astrocytes disposed therein;

a first plurality of fluid conduits fluidically coupling the inlet to the center well on the fluid flow side of the center well, such that the first plurality of fluid conduits span from the porous membrane of the inlet to the porous membrane of the center well; and a second plurality of fluid conduits fluidically coupling the outlet to the center well on the fluid flow side of the center well, such that the second plurality of fluid conduits span from the porous membrane of the center well to the porous membrane of the outlet, wherein the human endothelial cells and the astrocytes disposed on opposing sides of the porous membrane of the center well are configured to decrease a permeability of the porous membrane of the center well, thereby accurately modeling the blood-brain barrier, and wherein the center well, the inlet, the outlet, the first plurality of fluid conduits, and the second plurality of conduits form a closed loop system, such that an equilibrium of fluid flowing through the closed loop system is accomplished.

2. The device of claim 1, wherein a thickness of the porous membrane of the center well is approximately 120 μm.

3. The device of claim 1, wherein the porous membrane of the center well includes a plurality of pores each having a diameter of approximately 0.4 μm.

4. The device of claim 1, wherein the fluid flowing through the system between the center well, the inlet, and the outlet is a bidirectional flow.

5. The device of claim 1, wherein at least one of the first plurality of fluid conduits is arranged in an oscillating pattern, such that a length of the at least one of the first plurality of fluid conduits from a first end to a second end is greater than a distance between the inlet and the center well.

6. The device of claim 1, wherein each of the first plurality of fluid conduits is arranged in an oscillating pattern, such that a length of each of the first plurality of fluid conduits from a first end to a second end is greater than a distance between the inlet and the center well.

7. The device of claim 1, wherein at least one of the second plurality of fluid conduits is arranged in an oscillating pattern, such that a length of the at least one of the second plurality of fluid conduits from a first end to a second end is greater than a distance between the outlet and the center well.

8. The device of claim 1, wherein each of the second plurality of fluid conduits is arranged in an oscillating pattern, such that a length of each of the second plurality of fluid conduits from a first end to a second end is greater than a distance between the outlet and the center well.

9. The device of claim 1, wherein the device is disposed on an insert coupled to a chip including a plurality of testing wells, such that the device is configured to test the permeability of the porous membrane of the center well via a fluid transferred from the plurality of testing wells on the chip to the device on the insert.

10. An in vitro microfluidic device configured to model a blood-brain barrier, the microfluidic device comprising:

a microfluidic chip including a plurality of testing wells and an insert coupled to the microfluidic chip, the chip including a device including:

a center well in fluidic communication with each of an inlet and an outlet, each of the center well, inlet, and outlet including an independent bottom surface that is a porous membrane and a fluid containing portion extending away from the porous membrane;

the porous membrane of the center well separating a fluid flow side from the fluid containing portion, the fluid flow side configured to mimic a blood side of a blood-brain barrier, the fluid containing portion configured to mimic a brain side of the blood-brain barrier;

the fluid flow side of the porous membrane of the center well including a plurality of human endothelial cells disposed on the porous membrane, and the fluid containing portion of the center well including a plurality of astrocytes disposed therein;

a first plurality of fluid conduits fluidically coupling the inlet to the center well on the fluid flow side of the center well, such that the first plurality of fluid conduits span from the porous membrane of the inlet to the porous membrane of the center well; and a second plurality of fluid conduits fluidically coupling the outlet to the center well on the fluid flow side of the center well, such that the second plurality of fluid conduits span from the porous membrane of the center well to the porous membrane of the outlet, wherein the human endothelial cells and the astrocytes disposed on opposing sides of the porous membrane of the center well are configured to decrease a permeability of the porous membrane of the center well, thereby accurately modeling the blood-brain barrier, wherein the center well, the inlet, the outlet, the first plurality of fluid conduits, and the second plurality of conduits form a closed loop system, such that an equilibrium of fluid flowing through the closed loop system is accomplished, and wherein the device is configured to test the permeability of the porous membrane of the center well via a fluid transferred from the plurality of testing wells on the chip to the device on the insert.

11. The microfluidic device of claim 10, wherein a thickness of the porous membrane of the center well is approximately 120 μm.

12. The microfluidic device of claim 10, wherein the porous membrane of the center well includes a plurality of pores each having a diameter of approximately 0.4 μm.

13. The microfluidic device of claim 10, wherein at least one of the first plurality of fluid conduits is arranged in an oscillating pattern, such that a length of the at least one of the first plurality of fluid conduits from a first end to a second end is greater than a distance between the inlet and the center well.

14. The microfluidic device of claim 10, wherein at least one of the second plurality of fluid conduits is arranged in an oscillating pattern, such that a length of the at least one of the second plurality of fluid conduits from a first end to a second end is greater than a distance between the outlet and the center well.

15. An in vitro microfluidic device configured to model a blood-brain barrier, the microfluidic device comprising:

a chip including a plurality of testing wells and an insert coupled to the chip, the chip including a plurality of devices, each of the plurality of devices including:

a center well in fluidic communication with each of an inlet and an outlet, each of the center well, inlet, and outlet including an independent bottom surface that is a porous membrane and a fluid containing portion extending away from the porous membrane;

the porous membrane of the center well separating a fluid flow side from the fluid containing portion, the fluid flow side configured to mimic a blood side of a blood-brain barrier, the fluid containing portion configured to mimic a brain side of the blood-brain barrier;

the fluid flow side of the porous membrane of the center well including a plurality of human endothelial cells disposed on the porous membrane, and the fluid containing portion of the center well including a plurality of astrocytes disposed therein;

a first plurality of fluid conduits fluidically coupling the inlet to the center well on the fluid flow side of the center well, such that the first plurality of fluid conduits span from the porous membrane of the inlet to the porous membrane of the center well; and a second plurality of fluid conduits fluidically coupling the outlet to the center well on the fluid flow side of the center well, such that the second plurality of fluid conduits span from the porous membrane of the center well to the porous membrane of the outlet, wherein the human endothelial cells and the astrocytes disposed on opposing sides of the porous membrane of the center well are configured to decrease a permeability of the porous membrane of the center well, thereby accurately modeling the blood-brain barrier, wherein the center well, the inlet, the outlet, the first plurality of fluid conduits, and the second plurality of conduits form a closed loop system, such that an equilibrium of fluid flowing through the closed loop system is accomplished, and wherein each of the plurality of devices is configured to test the permeability of the porous membranes of the center wells via a fluid transferred from the plurality of testing wells on the chip to each of the plurality of devices on the insert.

16. The microfluidic device of claim 15, wherein, for each of the plurality of devices, each of the first plurality of fluid conduits is arranged in an oscillating pattern, such that a length of each of the first plurality of fluid conduits from a first end to a second end is greater than a distance between the inlet and the center well.

17. The microfluidic device of claim 15, wherein, for each of the plurality of devices, each of the second plurality of fluid conduits is arranged in an oscillating pattern, such that a length of each of the second plurality of fluid conduits from a first end to a second end is greater than a distance between the outlet and the center well.

* * * * *